United States Patent [19]

Weltman

[11] 4,251,445
[45] Feb. 17, 1981

[54] N-SUCCINIMIDYL HALOACETYL AMINOBENZOATES AS COUPLING AGENTS

[76] Inventor: Joel K. Weltman, 164 Summit Ave., Providence, R.I. 02906

[21] Appl. No.: 93,607

[22] Filed: Nov. 13, 1979

Related U.S. Application Data

[62] Division of Ser. No. 889,726, Mar. 24, 1978, Pat. No. 4,218,539.

[51] Int. Cl.³ .......................................... C07D 207/46
[52] U.S. Cl. ................................................. 260/326.4
[58] Field of Search ..................................... 260/326.4

[56] References Cited

U.S. PATENT DOCUMENTS 3,541,084  11/1970  Hagitani et al. .................. 260/326.4

FOREIGN PATENT DOCUMENTS 42-26865  11/1969  Japan ..................................... 260/326.4
47-416    1/1972   Japan ..................................... 260/326.4

OTHER PUBLICATIONS

W. Higgins et al., Chem. Abstracts 89: 142590d, (1978).
D. Santi et al., Chem. Abstracts 83: 175111c, (1975).
T. Kitagawa et al., J. Biochem., 79, 233-236, (1976). Enzyme Coupled Immunoassay of Insulin Using a Novel Coupling Reagent.

*Primary Examiner*—Donald G. Daus
*Assistant Examiner*—M. C. Eakin
*Attorney, Agent, or Firm*—Richard P. Crowley

[57] ABSTRACT

Novel enzyme conjugates useful in immunoassay methods are prepared with the use of a novel coupling reagent of N-succinimidyl (4-iodoacetyl) aminobenzoate by reacting the coupling reagent, firstly, with an amino-containing macromolecule, and, thereafter, with a sulfhydryl-containing enzyme, the enzyme conjugate prepared in a high yield and of high specificity.

4 Claims, No Drawings

N-SUCCINIMIDYL HALOACETYL AMINOBENZOATES AS COUPLING AGENTS

This is a division of application Ser. No. 889,726, filed on Mar. 24, 1978, now U.S. Pat. No. 4,218,539.

BACKGROUND OF THE INVENTION

Enzyme-macromolecule conjugates are typically used for the detection and determination of substances present in very low quantities; for example, nanogram quantities of substances in biological fluids, such as urine and serum. A wide variety of enzymes may be used to form the conjugate, but the enzymes selected are often those enzymes which can be detected with great sensitivity. The macromolecular portion of the conjugate presents a wide variety of amino-containing compounds, including, but not limited to, nucleic acids, proteins, hormones, antigens and allergens, which are characterized in containing amino groups.

Enzymes conjugates are prepared in a conjugation reaction with a polyfunctional coupling reagent which links the enzyme and macromolecule together by reaction with one or more of the reactive groups in the reactants. In the preparation of enzyme conjugates, it is most desirable to produce enzyme conjugates of high stability, high specificity and good reproducibility.

In some coupling reactions to prepare enzyme conjugates, it has been suggested to employ a conditioner compound, such as a polyamine, to improve specificity of the enzyme conjugate, with resulting improvement in the detection method due to low signal-to-noise ratio during detection in the immunochemical test. The preparation of enzyme conjugates, employing prior-art coupling reagents with conditioners, is described in U.S. Pat. No. 4,002,532, issued Jan. 1, 1977, hereby incorporated by reference.

A new coupling agent has been described for the preparation of an enzyme-coupled insulin conjugate for use in the immunoassay of insulin. The coupling agent is meta-maleimidobenzoyl N-hydroxysuccinimide ester (MBS), a bifunctional reagent which acylates the amino groups of the insulin by reaction with the N-hydroxysuccinimide ester group and by forming thioester bonds with the enzyme by addition of the thiol groups to the maleimide group. This coupling agent has been employed in preparing an enzymatically active and immuno-reactive B-D-galactosidase-MBS-insulin conjugate (see *J.Biochem.*, 79, 233-236 (1976), "Enzyme Coupled Immunoassay of Insulin Using a Novel Coupling Reagent", Kitagawa, T and Aikawa, T, hereby incorporated by reference). Although the MBS coupling reagent is satisfactory in some respects, it is desirable to obtain enzyme conjugates of greater stability and greater specificity and sensitivity.

SUMMARY OF THE INVENTION

My invention relates to novel coupling reagents and their method of preparation, which reagents are useful in the preparation of stable enzyme conjugates, to the method of preparing the enzyme conjugates employing my coupling reagents, and to the use of such enzyme conjugates in immunoassay methods.

My polyfunctional class of coupling reagents, to form enzyme conjugates with a high yield and specific activity, comprises, in the generic sense, a reagent which reacts, firstly, with the amino groups of the macromolecule and then with the sulfhydryl groups in the enzyme, and are represented by the formula:

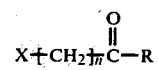

where X is a halogen, preferably iodine; n is a whole number of from about 1 to 8, preferably 1 to 4; and R represents any radical which is capable of reacting with the amino groups of the macromolecule, such radical including, but not being limited to:

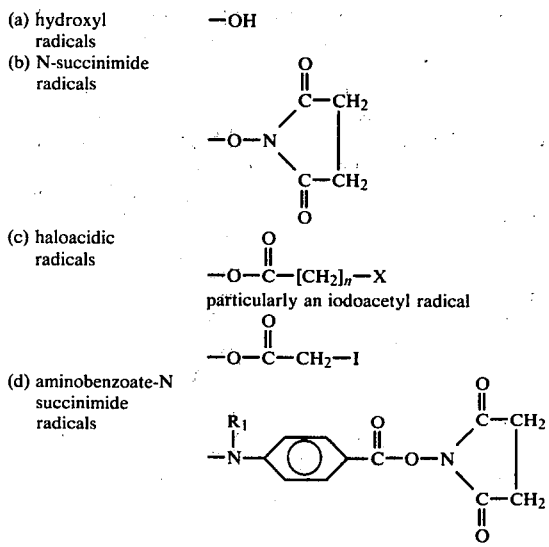

wherein $R_1$ is hydrogen or an alkyl group, such as methyl.

Other amino-reacting groups may be employed as the R radical.

The most preferred coupling reagent is N-succinimidyl (4-iodoacetyl) aminobenzoate (SIAB) having the structural formula:

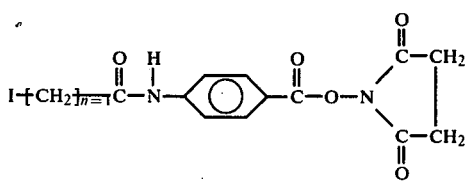

The SIAB reagent produces enzyme conjugates with unexpectedly high yields and specific immunochemo, enzyme and conjugate activity. Enzyme conjugates prepared with SIAB, in comparison to other prior art coupling reagents, such as MBS, provide enzyme conjugates of high stability and high specific conjugate yields.

Specific useful coupling reagents include, but are not limited to: iodoacetic acid; iodoacetic anhydride; and N-hydroxysuccinimide ester of iodoacetic acid.

Iodoacetic acid reacts with $-NH_2$ groups in the presence of a water-soluble carbodiimide, such as 1-ethyl-3-(3-dimethylaminopropyl) carbodiimide. Iodoacetic anhydride reacts directly with $-NH_2$ groups. In the other cases, my coupling reagents are prepared by reacting the selected halo organic acid or acid anhydride in a solvent with the R amino-reacting portion of the molecule, and the reagent is then recovered. For example, SIAB is synthesized by reaction of iodoacetic anhydride with paraaminobenzoic acid in an organic solvent, such as dioxane. The resultant intermediate compound is crystallized and the active ester is formed between the intermediate and N-hydroxysuccinimide, with a carbodiimide in an organic solvent; for example, with dicyclohexylcarbodiimide in tetrahydrofuran. The resultant product, which may be crystallized, is SIAB.

The enzyme conjugates of my invention are prepared by a conjugate reaction between the amino-reacting substituent of my coupling reagent and the macromolecule, and, thereafter, reacting the halo-reacting agent with the sulfhydryl groups of the enzyme. It is essential in the preparation of my enzyme conjugates that the reaction sequence be, firstly, the reaction of the R amino-reacting group, such as the succinimidyl group, with the amino group of the protein or other macromolecule, and, thereafter, reaction of X with sulfhydryl groups of the enzyme; otherwise, the R group would react with the amino group of the enzyme, resulting in lower yields and a lack of specificity in the resulting enzyme conjugate product so prepared.

For example, my coupling reagent provides for the preparation of an enzyme conjugate with a high degree of specific coupling, as represented by the following illustrative reaction with SIAB:

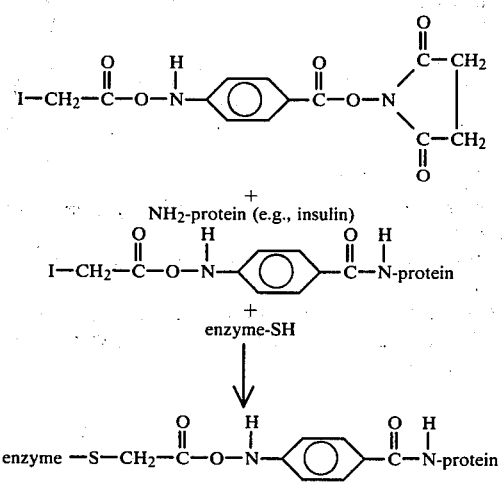

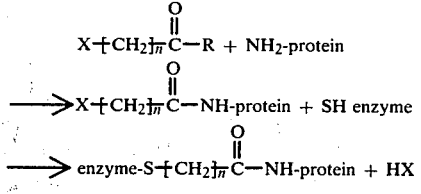

Typically SIAB is reacted in an aqueous solution with amino groups of the macromolecules under mild conditions. For example, SIAB is reacted with immunoglobulin in 0.5 M phosphate buffer, pH 7.0. The resultant immunoglobulin derivative is then reacted with an enzyme which contains sulfhydryl groups. One such enzyme is Beta D galactosidase (BG) isolated from E. coli. BG is reacted with the derivatized immunoglobulin under mild aqueous conditions. The resulting BG macromolecule conjugates so prepared with my coupling reagent have a high degree of enzyme activity, immunological specificity, and are obtained in extremely high yields; for example, virtually all the immunoglobulin or other macromolecule and BG are stoichiometrically conjugated to each other. The yield of BG conjugate so achieved is surprisingly high. The conjugates of BG with either antigens or antibodies produced with SIAB are useful in enzyme immunoassays for various antigens or antibodies, including hepatitis, serum proteins, hormones and drugs:

Any SH-reactive enzyme may be used in my method, such as, for example, acid and alkaline phosphatases, alcohol dehydrogenase catalase, glucose and galactose oxidases, a- and B-galactosidases, lactate dehydrogenase, lysozyme, luciferase, peroxidases, ribonuclease, rodhanase and esterases.

Useful $NH_2$-reactive macromolecules include deoxy and ribonucleic acids, viral proteins, allergens, immunoglobulins, blood groups substances, transplantation antigens, carcino embryonic antigen, alpha-fetoprotein and other tumor specific antigens, growth hormones and other polypeptide hormones.

The SIAB is particularly useful in the preparation of immunoglobulin-bacterial enzyme B-D-galactosidase conjugates. The enzyme conjugates of the invention are used for the detection of antigens, antibodies, allergens, hormones and other macromolecules in low nanogram, or less, quantities by immunoassay techniques.

My unique enzyme conjugates find particular use in those test experiments and detection techniques relating to macromolecules, particularly to the detection and determination of nanogram quantities of substances in biological fluids, such as the detection of antibodies, antigens, allergens, hormones and the like. In particular my SIAB enzyme conjugates find use in enzyme immunoassay techniques for hepatitis. In prior-art techniques, repeated washings of the patient's serum on the solid support; that is, an antigen disc, are required to remove nonspecific, absorbed serum proteins. However, the use of SIAB conjugate enzymes makes feasible a one-step enzyme immunoassay method. Limited washing or no washing is possible with my SIAB enzyme conjugates, since all or substantially all of the specific-form enzyme is bound to the antibody.

My enzyme conjugates may be employed in the prior-art techniques for the detection of antibodies; for example, as set forth in U.S. Pat. No. 4,002,532 (supra) wherein the detection method comprises adhering, such as by absorption, to a solid support or absorbent material, such as a disc, which binds or absorbs the antibodies or other macromolecules to be detected; adding to the solid support material a fluid, such as serum or urine, to bind the antibodies therein to the support material used; for example, incubating the serum with the disc; washing the support material to remove unbound components of the fluid, such as nonspecifically bound and absorbed serum proteins, from the disc surface, adding the enzyme conjugate to the washed support, such as by incubation of the disc with an enzyme-active SIAB protein conjugate, so that the specific enzyme conjugate is bound to the support in proportion to the quantity of disc-bound antibodies, and thus is a measure of the patient's IgE or other macromolecules to be quantitated; optionally washing the support to remove unbound unspecific enzyme conjugate from the support disc; and determining the enzymatic activity of the bound enzyme conjugate as a measure of the amount of bound antibodies.

In such a detection method, the high specific yield of my enzyme conjugate provides for a high degree of coupling with the support material in comparison to prior-art techniques, as indicated, for example, in the unexpectedly high signal-to-noise ratio in the detection method; that is, the enzyme conjugates of my invention increase sensitivity and specificity by specific bonding of the enzyme conjugate to the solid support, and permit increased sensitivity in the detection of antibodies with lower quantities of enzyme conjugates and in the presence of interfering substances not possible in the prior-art enzyme conjugates. For example, when employing the SIAB coupling reagent with a human serum containing a known amount of antigen, the enzyme conjugate is quite stable, and a determination of the amount of bound enzyme is about three and one-half times more than with the MBS coupling reagent at about one-half the amount of enzyme to provide a specific conjugate with an improvement of about 15 fold.

My invention will be illustrated by specific and preferred examples; however, it is recognized that various changes and modifications can be made in such examples without departing from the spirit and scope of my invention.

DESCRIPTION OF SPECIFIC EMBODIMENTS

EXAMPLE 1

Preparation of SIAB Coupling Reagent

N-succinimidyl (4-iodoacetyl) aminobenzoate (SIAB), the preferred coupling reagent of my invention, was prepared by the following reaction:

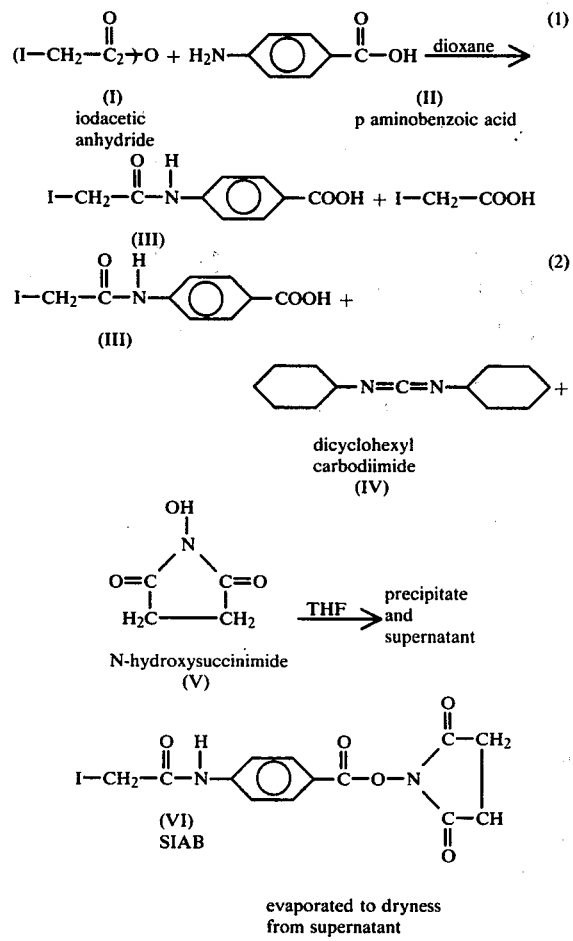

EXAMPLE 2

Preparation of SIAB Enzyme Conjugates 354 mg of cpd I ($10^3$ μmoles) were dissolved in 5 ml dioxane and added to 68.6 mg of cpd II (500 μmoles) in 2.5 ml of dioxane and were reacted for 5 hours at room temperature (20°–25° C.) in the dark and then at 4° C. for 2 days. A white flocculent precipitates (cpd III) was isolated by centrifugation and triturated with ether (0.5 ml) three times. The resulting white powder was dried with hot air with a yield of 160 mg. Cpd III (128 mg; $4 \times 4^{-4}$ moles) and cpd IV (86.2 mg; $4 \times 10^{-4}$ moles) were dissolved and reacted in tetrahydrofuran THF (3.35 ml) at 4° C. for 20 hours. A precipiate was removed and the supernatant liquid was recovered and evaporated to dryness and triturated with ether, and pale yellow crystals were recovered of impure SIAB (cpd VI), yield 135 mg (79.5% yield), mp 172°–175° C. The impure cpd VI was recrystallized from methyl alcohol and was washed twice with diethyl ether to provide white crystals of SIAB having an mp of 194° to 196° C. (decomp). Confirmation of this SIAB composition was made by elemental analysis.

Rabbit antibodies against sheep immunoglobulin (RaShIg) were conjugated to beta-D-galactosidase (BG) with SIAB to provide an enzyme antibody conjugate. The purified RaShIg and the BG were obtained as set forth in Example 1, U.S. Pat. No. 4,002,532. A mixture of RaShIg (3.9 mg, $2.63 \times 10^{-8}$ moles) and SIAB (30λ of 3.6 mg/ml of THF) was prepared in an aqueous 0.05 M sodium-phosphate-buffered solution (pH 7.0) and the mixture was permitted to react at room temperature overnight; that is, 12 hours in the dark, to provide an acylated RaShIg product, with some of the amino groups of the antibodies reacted with the active succinimidyl group of the SIAB coupling reagent. The reaction was quenched by the addition of glycine (30λ, $4.5 \times 10^{-2}$ moles) to the acylated RaShIg for 3 hours at room temperature in the dark. To the quenched RaShIg was added BG (25× molar excess of RaShIg over BG), with the solution adjusted to a pH of 7.8 at 4° C. for 2 days. Thereafter, the reaction of the iodine radical with the sulfhydryl of the enzyme BG was quenched by the addition of 2-mercaptoethanol ($4 \times 10^{-3}$ M), and the mixture was maintained at room temperature for 3 hours. The RaShIg-BG conjugate so obtained was diluted, clarified and recovered. There was not detectable loss in activity of enzyme as a result of the coupling procedure.

EXAMPLE 3

Preparation of Iodoacetyl N-Succinimide (INS)

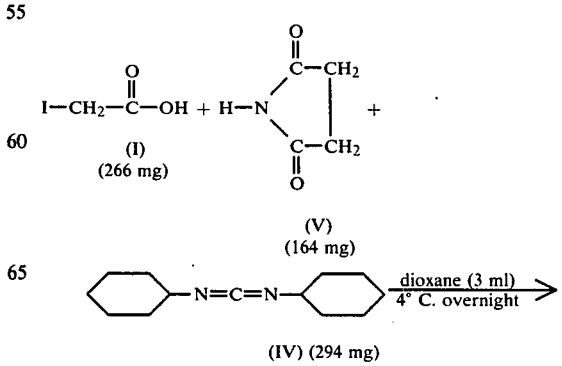

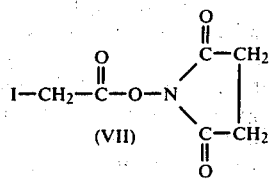

(VII)

EXAMPLE 4

Comparison of RaShIg-BG Conjugates

The conjugate so prepared was prepared in a buffered enzyme solution of standard units (10,000) of enzyme activity per ml and tested, as in U.S. Pat. No. 4,002,532 (column 5, line 55–column 6, line 1), to determine that the conjugate exhibited a high degree of specificity as illustrated by the S/N ratio shown in the table below, when compared with the same conjugates prepared in a similar manner, but with prior-art coupling agents MBS and W-R agent (see U.S. Pat. No. 4,002,532, Example 1).

TABLE I

Comparison of S/N of Sheep Immunoglobulin (ShIg) Conjugates of Beta Galactosidase (BG)

| Units of ShIg-BG Added Per Disc | Coupling Reagent | | |
|---|---|---|---|
| | SIAB* | MBS* | W-R |
| 1 | 94 ± 7 | 41 ± 1 | 67 ± 4 |
| 10 | 63 ± 2 | 58 ± 1 | 52 ± 2 |
| 100 | 32 ± 2 | 18 ± 0 | 20 ± 1 |

*Numbers are S/N ± standard deviation of duplicate measurements. S is binding to immuno specific RaShIg discs. N is binding to normal nonspecific Rabbit RIg discs.

The maximum S/N ratio for SIAB is almost twice the S/N for the MBS coupling agent, and the S/N for SIAB was rising monotonically while the MBS S/N went through a maximum value. Thus, SIAB conjugates could be used at even lower than unit concentrations to provide even better S/N ratios. The S/N ratios establish that the SIAB conjugates are highly specific in comparison to prior-art conjugates. This is borne out by a comparison of SIAB and W-R conjugates in a test for $HB_sAg$ (Table II).

TABLE II

Comparison of Conjugates* of Beta Galactosidase (BG) in a Test for Hepatitis B-Surface Angiten ($HB_sAg$)

| $HB_sAg$ (ng) | SIAB** | W-R** | SIAB/W-R |
|---|---|---|---|
| 0 | 0 | 0 | — |
| 0 | 0 | 0 | — |
| 3.13 | .00462 | .00115 | 4.02 |
| 3.13 | .00322 | .00196 | 1.64 |
| 6.25 | .00815 | .00226 | 3.61 |
| 6.25 | .00645 | .00156 | 4.13 |
| 12.50 | .01435 | .00786 | 1.83 |
| 12.50 | .01275 | .00766 | 1.66 |
| 25.00 | .02035 | .01376 | 1.55 |
| 25.00 | .02145 | .01396 | 1.54 |

*Conjugates are Rabbit anti-goat Ig coupled to beta galactosidase used to detect goat anti-$HB_sAg$.
**Numbers are units of BG bound to each immunosorbent disc.

The average SIAB/W-R is 2.5; that is, an average of 2.5 times more SIAB conjugate was specifically bound. The procedure followed was that set forth in the Weltman et al patent (supra).

What I claim is:

1. A compound suitable for use as a coupling reagent to form enzyme conjugates, of the formula:

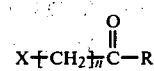

wherein X is a halogen; n is a whole number of from 1 to 8; and R is an amino-reactive group having the formula of:

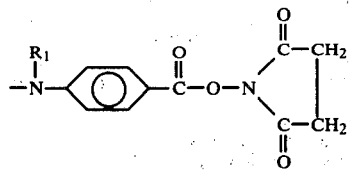

wherein $R_1$ is a hydrogen or a lower alkyl group.

2. The compound of claim 1 wherein $R_1$ is a methyl group.

3. The compound of claim 1 wherein X is an iodo group.

4. The compound of claim 1, which compound is N-succinimidyl (4-iodoacetyl) aminobenzoate.

* * * * *